(12) United States Patent
Charifson et al.

(10) Patent No.: US 8,202,889 B2
(45) Date of Patent: Jun. 19, 2012

(54) INHIBITORS OF BACTERIAL IMPDH

(75) Inventors: Paul Charifson, Framingham, MA (US);
Trudy Grossman, Lexington, MA (US);
Emanuele Perola, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 946 days.

(21) Appl. No.: 11/517,755

(22) Filed: Sep. 8, 2006

(65) Prior Publication Data
US 2007/0191434 A1    Aug. 16, 2007

Related U.S. Application Data

(60) Provisional application No. 60/715,459, filed on Sep. 9, 2005.

(51) Int. Cl.
*A61K 31/44* (2006.01)
*A61K 31/41* (2006.01)
*A61K 31/425* (2006.01)

(52) U.S. Cl. ........ 514/332; 514/345; 514/352; 514/371; 514/363

(58) Field of Classification Search ........... 514/332, 514/352, 376
See application file for complete search history.

(56) References Cited

U.S. PATENT DOCUMENTS

| | | | | |
|---|---|---|---|---|
| 6,693,108 B2 * | 2/2004 | Green et al. | .......... | 514/275 |
| 2005/0130974 A1 * | 6/2005 | Ramesh et al. | .......... | 514/248 |
| 2005/0137234 A1 | 6/2005 | Bressi et al. | | |

FOREIGN PATENT DOCUMENTS

| | | |
|---|---|---|
| WO | 99/55663 | 11/1999 |
| WO | 2005/118579 | 12/2005 |
| WO | 2006/013209 | 2/2006 |

OTHER PUBLICATIONS

International Search Report from the counterpart PCT application.

* cited by examiner

*Primary Examiner* — Shengjun Wang
(74) *Attorney, Agent, or Firm* — Michael C. Badia

(57) ABSTRACT

The present invention relates to methods of inhibiting bacterial IMPDH comprising administering compounds of formula I:

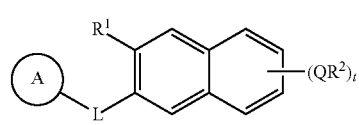

or pharmaceutically acceptable salts thereof. The present invention also relates to pharmaceutically acceptable compositions comprising said compounds. These compounds, and compositions thereof, are useful in treating bacterial infections.

1 Claim, No Drawings

INHIBITORS OF BACTERIAL IMPDH

CROSS REFERENCE TO RELATED APPLICATIONS

This application claims the benefit, under 35 U.S.C. §119, of U.S. provisional patent application No. 60/715,459, filed Sep. 9, 2005, which is hereby incorporated by reference.

FIELD OF THE INVENTION

The present invention relates to compounds that inhibit bacterial IMPDH. This invention also relates to pharmaceutical compositions comprising these compounds. The compounds and pharmaceutical compositions of this invention are useful for inhibiting bacterial IMPDH. The present invention also relates to methods for treating bacterial infections in mammals.

BACKGROUND OF THE INVENTION

The synthesis of nucleotides in organisms is required for the cells in those organisms to divide and replicate. Nucleotide synthesis in mammals may be achieved through one of two pathways: the de novo synthesis pathway or the salvage pathway. Different cell types use these pathways to a different extent.

Inosine-5'-monophosphate dehydrogenase (IMPDH; EC 1.1.1.205) is an enzyme involved in the de novo synthesis of guanosine nucleotides. IMPDH catalyzes the NAD-dependent oxidation of inosine-5'-monophosphate (IMP) to xanthosine-5'-monophosphate (XMP)[Jackson R. C. et. al., Nature, 256, pp. 331-333, (1975)].

IMPDH is ubiquitous in eukaryotes, bacteria and protozoa [Y. Natsumeda & S. F. Carr, Ann. N.Y. Acad., 696, pp. 88-93 (1993)]. The prokaryotic forms share 30-40% sequence identity with the human enzyme. Regardless of species, the enzyme follows an ordered Bi—Bi reaction sequence of substrate and cofactor binding and product release. First, IMP binds to IMPDH. This is followed by the binding of the cofactor NAD. The reduced cofactor, NADH, is then released from the enzyme, followed by the product, XMP [S. F. Carr et al., J. Biol. Chem., 268, pp. 27286-90 (1993); E. W. Holmes et al., Biochim. Biophys. Acta, 364, pp. 209-217 (1974)]. This mechanism differs from that of most other known NAD-dependent dehydrogenases, which have either a random order of substrate addition or require NAD to bind before the substrate.

Two isoforms of human IMPDH, designated type I and type II, have been identified and sequenced [F. R. Collart and E. Huberman, J. Biol. Chem., 263, pp. 15769-15772, (1988); Y. Natsumeda et. al., J. Biol. Chem., 265, pp. 5292-5295, (1990)]. Each is 514 amino acids, and they share 84% sequence identity. Both IMPDH type I and type II form active tetramers in solution, with subunit molecular weights of 56 kDa [Y. Yamada et. al., Biochemistry, 27, pp. 2737-2745 (1988)].

The de novo synthesis of guanosine nucleotides, and thus the activity of IMPDH, is particularly important in B and T-lymphocytes. These cells depend on the de novo, rather than salvage pathway to generate sufficient levels of nucleotides necessary to initiate a proliferative response to mitogen or antigen [A. C. Allison et. al., Lancet II, 1179, (1975) and A. C. Allison et. al., Ciba Found. Symp., 48, 207, (1977)]. Thus, IMPDH is an attractive target for selectively inhibiting the immune system without also inhibiting the proliferation of other cells.

It is also known that IMPDH plays a role in other metabolic events. Increased IMPDH activity has been observed in rapidly proliferating human leukemic cell lines and other tumor cell lines, indicating IMPDH as a target for anti-cancer as well as immunosuppressive chemotherapy [M. Nagai et. al., Cancer Res., 51, pp. 3886-3890, (1991)]. IMPDH has also been shown to play a role in the proliferation of smooth muscle cells, indicating that inhibitors of IMPDH, such as MPA or rapamycin, may be useful in preventing restenosis or other hyperproliferative vascular diseases [C. R. Gregory et al., Transplantation, 59, pp. 655-61 (1995); PCT publication WO 94/12184; and PCT publication WO 94/01105].

IMPDH has also been shown to play a role in viral replication in some viral cell lines. [S. F. Carr, J. Biol. Chem., 268, pp. 27286-27290 (1993)]. Analogous to lymphocyte and tumor cell lines, the implication is that the de novo, rather than the salvage, pathway is critical in the process of viral replication.

Additionally, the de novo synthesis of purine nucleotides, and thus the activity of IMPDH, is implicated in attenuating bacterial growth and virulence under purine starved conditions. Several biological lines of evidence exist suggesting that IMPDH could be a selective antibacterial target. Biological fluids are low in free purines and therefore limiting for bacterial growth [Simmonds et al., Techniques in Diag. Huma. Biochem. Gen.: A Lab Manual, pp. 397-424 (1991)]. Several independent studies have shown that purine auxotrophy attenuates virulence of Salmonella strains, Shigella flexniri, E. coli and E. faecalis [MacFarland and Stocker, Microb. Path., 3, pp. 129-141 (1987); Russo et al., Mol. Microb., 22, pp. 217-229 (1996); Mahan et al., Science, 259, pp. 686-688 (1993); Singh et al., J. Infect. Dis., 178, pp. 1416-1420 (1998); Fields et al., PNAS, 83, pp. 5189-5193 (1986); Noriega et al., Infect. Immun., 64, pp. 3055-3061 (1996)]. This was specifically shown for guaB mutants of Salmonella and Shigella which were defective in the gene encoding IMPDH [MacFarland and Stocker, Microb. Path., 3, pp. 129-141 (1987) and Noriega et al., Infect. Immun., 64, pp. 3055-3061 (1996)].

Additional evidence exists for significant differences between mammalian IMPDH and bacterial IMPDH suggesting that IMPDH is an attractive target for selectively inhibiting bacterial growth without also inhibiting mammalian IMPDH functions. For instance, known mammalian IMPDH inhibitors such as mycophenolic acid are >1000-fold less potent against bacterial IMPDH versus mammalian IMPDH [Hedstrom et al., Curr. Med. Chem., 6, pp. 545-560 (1999)]. This is an example of "reverse selectivity" from an antibacterial standpoint and suggests that significant differences exist between the mammalian and bacterial enzymes. This "reverse selectivity" has been shown in part to be due to residue differences in the NAD site and in part due to differences in kinetic mechanism [Hedstrom et al., Biochemistry, 38, pp. 15388-15397 (1999); Hedstrom et al., Biochemistry, 39, pp. 1771-1777 (2000)]. These differences can be exploited to design inhibitors that are selective for bacterial IMPDH over mammalian IMPDH.

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as Streptococcus pneumoniae (SP), Mycobacterium tuberculosis, and Enterococcus. The appearance of vancomycin resistant enterococcus was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., *Current Opinion in Anti-infective Investigational Drugs*, 1999, 1, 1; Levy, "The Challenge of Antibiotic Resistance", *Scientific American*, March, 1998).

As bacterial resistance to antibiotics has become an important public health problem, there is a continuing need to develop newer and more potent antibiotics. More particularly, there is a need for antibiotics that represent a new class of compounds not previously used to treat bacterial infection. One attractive strategy for developing new antibiotics is to inhibit bacterial IMPDH, a bacterial enzyme necessary for the de novo synthesis of purine nucleotides, and therefore, necessary for bacterial cell growth and division.

SUMMARY OF THE INVENTION

It has now been found that compounds of this invention, and pharmaceutically acceptable compositions thereof, are useful as inhibitors of bacterial IMPDH. These compounds can be used alone or in combination with other antibiotic agents for the treatment of bacterial infections.

In one embodiment, the invention provides a method of inhibiting bacterial IMPDH in a patient, comprising administering to said patient a therapeutically effective amount of a compound of formula I:

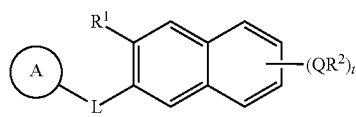

or a pharmaceutically acceptable salt thereof, wherein $R^1$, $R^2$, Q, L, t, and Ring A are as defined below.

In another embodiment, the invention provides a method of inhibiting bacterial IMPDH to decrease bacterial quantity in a patient, comprising administering to said patient a therapeutically effective amount of a compound of formula I.

In yet another embodiment, the invention provides a method of inhibiting bacterial IMPDH to treat or lessen the severity of a bacterial infection in a patient, comprising administering to said patient a therapeutically effective amount of a compound of formula I.

In yet another embodiment, the invention provides a method of inhibiting bacterial IMPDH, comprising contacting bacteria with a compound of formula I.

In still another embodiment, the invention provides a pharmaceutical composition comprising a pharmaceutically acceptable carrier, adjuvant, or vehicle and a compound of formula I.

These compounds, and pharmaceutically acceptable compositions thereof, are useful for treating or lessening the severity of bacterial infections. In particular, the compounds of the present invention are useful in treating or lessening the severity of urinary tract infections, pneumonia, prostatitis, skin and soft tissue infections, intra-abdominal infections, blood stream infections, or infections of febrile neutropenic patients.

DESCRIPTION OF THE INVENTION

In one embodiment, the present invention provides a method of inhibiting bacterial IMPDH in a patient, comprising administering to said patient a therapeutically effective amount of a compound of formula I:

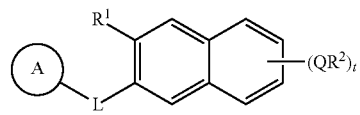

or a pharmaceutically acceptable salt thereof, wherein:

Ring A is a 5-6 membered heteroaryl ring or a 4-7 membered saturated or partially unsaturated heterocyclic ring each ring having 1-4 heteroatoms independently selected from N, $NR^3$, O, S, SO, or $SO_2$;

wherein said 5-6 membered heteroaryl ring system is optionally linearly fused to a second 5-6 membered aryl or heteroaryl ring or optionally linearly fused to a 4-7 membered saturated or partially unsaturated heterocyclic or carbocyclic ring;

wherein said 5-6 membered aryl or heteroaryl fused ring contains 0-3 heteroatoms independently selected from N, O, or S;

wherein said 4-7 membered fused ring contains 0-3 heteroatoms independently selected from N, $NR^3$, O, S, SO, or $SO_2$;

wherein said 4-7 membered saturated or partially unsaturated heterocyclic ring is optionally linearly fused to a second 5-6 membered aryl or heteroaryl ring or optionally spirocyclic bound to a 4-7 membered saturated or partially unsaturated heterocyclic or carbocyclic ring;

wherein said 5-6 membered aryl or heteroaryl fused ring contains 0-3 heteroatoms independently selected from N, O, or S;

wherein said 4-7 membered spirocyclic ring contains 0-3 heteroatoms independently selected from N, $NR^3$, O, S, SO, or $SO_2$; and wherein any of said rings is optionally substituted with up to 2 substituents independently selected from J;

J is —($C_1$-$C_4$)-straight or branched alkyl chain, —($C_2$-$C_4$)-straight or branched alkenyl or alkynyl, halogen, -(T)$_y$-Ar, -(T)$_y$-R', —$CF_3$, —$OCF_3$, oxo, —C(O)R', —C(O)C(O)R', —$CO_2$R', —OR', —N(R')$_2$, —SR', —$NO_2$, —CN, —C(O)N(R')$_2$, —OC(O)N(R')$_2$, —NR' C(O)R', —NR'C(O)N(R')$_2$, —N(OR')R', —C(=NOR')R', —$SO_2$R', —$SO_2$N(R')$_2$, —NR'$SO_2$R', —P(O)R')$_2$, —P(O)(OR')$_2$, or —OP(O) (OR')$_2$; wherein y is 0 or 1;

T is a ($C_1$-$C_4$)-straight or branched alkyl chain, wherein one methylene unit of T is optionally replaced by —O—, —C(O)—, —NH—, or —S—;

each R' is independently selected from hydrogen, a ($C_1$-$C_4$)-straight or branched alkyl chain, or a 5-6 membered saturated, unsaturated, or aryl ring having 0-3 heteroatoms independently selected from N, O, or S; or two R' groups together with the nitrogen to which they are bound optionally form a 3-6 membered heterocyclic ring; and each R' is substituted with 0-3 groups independently selected from halogen, oxo, $R^0$, $N(R^0)_2$, $OR^0$, $CO_2R^0$, $NR^0C(O)R^0$, $C(O)N(R^0)_2$, $SO_2R^0$, $SO_2N(R^0)_2$, or $NR^0SO_2R^0$; wherein
  each $R^0$ is independently selected from hydrogen, a ($C_1$-$C_4$)—straight or branched alkyl chain, or a 5-6 membered saturated, unsaturated, or aryl ring having 0-3 heteroatoms independently selected from N, O, or S;
  two substituents on adjacent positions of any ring may be taken together to form a 5-7 membered saturated, partially unsaturated, heterocyclic or carbocyclic ring or 5-6 membered aryl or heteroaryl ring, each ring having 0-3 heteroatoms independently selected from N, O, or S;
  Ar is a 3-8 membered saturated or unsaturated carbocyclic ring, a 5-6 membered aryl ring, a 3-7 membered heterocyclic ring having 1-3 heteroatoms independently selected from N, $NR^3$, O, S, SO, or $SO_2$, or a 5-6 membered heteroaryl ring having 1-4 heteroatoms independently selected from N, O, or S, wherein:
    Ar is optionally substituted with 1-3 J groups; and
    $R^3$ is hydrogen, —($C_1$-$C_4$)-straight or branched alkyl, —($C_2$-$C_4$)-straight or branched alkenyl or alkynyl, -(T)$_y$-Ar, C(O)R', $CO_2R'$, OR', N(R')$_2$, C(O)N(R')$_2$, NR'C(O)R', $SO_2R'$, $SO_2N(R')_2$, or NR'$SO_2R'$;
L is —C(O)N($R^4$), —N($R^4$)C(O), or a bond; wherein
  $R^4$ is selected from hydrogen or —($C_1$-$C_3$)-straight or branched alkyl;
$R^1$ is selected from hydrogen, halogen, $OR^5$, or N($R^5$)$_2$; wherein
  each $R^5$ is independently hydrogen, —($C_1$-$C_4$)-straight or branched alkyl, —($C_2$-$C_4$)-straight or branched alkenyl or alkynyl, or C(O)R';
Q is a bond or a —($C_1$-$C_3$)-straight or branched alkyl chain wherein one methylene unit of Q is optionally replaced by —$NR^+$—, —S—, —O—, —C(S)—, —$CO_2$—, —OC(O)—, —C(O)—, —C(O)C(O)—, —C(O)$NR^+$—, —$NR^+$C(O)—, —$NR^+CO_2$—, —$SO_2NR^+$—, —$NR^+SO_2$—, —C(O)$NR^+NR^+$—, —$NR^+$C(O)$NR^+$—, —OC(O)$NR^+$—, —$NR^+$—$NR^+$—, —$NR^+SO_2NR^+$—, —S(O)—, —$SO_2$—, —P(O)—, —$PO_2$—, or —P(O)$R^+$—;
  wherein $R^+$ is independently hydrogen, —($C_1$-$C_4$)-straight or branched alkyl, or —($C_2$-$C_4$)-straight or branched alkenyl or alkynyl optionally substituted with 1-3 groups independently selected from halogen, oxo, $R^0$, N($R^0$)$_2$, $OR^0$, $CO_2R^0$, $NR^0C(O)R^0$, $C(O)N(R^0)_2$, $SO_2R^0$, $SO_2N(R^0)_2$, or $NR^0SO_2R^0$;
t is 0-2; and
$R^2$ is hydrogen, —($C_1$-$C_3$)-straight or branched alkyl, —($C_2$-$C_4$)-straight or branched alkenyl or alkynyl, halogen, $NO_2$, $CF_3$, CN, or $Ar^1$;
  wherein $Ar^1$ is a 3-7 membered monocyclic or a 6-12 membered bicyclic saturated or partially unsaturated carbocyclic ring, a 5-6 membered monocyclic or a 7-11 membered bicyclic aryl ring, a 3-7 membered monocyclic or a 6-12 membered bicyclic heterocyclic ring having 1-5 heteroatoms independently selected from N, $NR^3$, O, S, SO, or $SO_2$, or a 5-6 membered heteroaryl ring having 1-4 heteroatoms independently selected from N, O, or S;
    wherein said 5-6 membered monocyclic or 7-11 membered bicyclic aryl ring or 5-6 membered heteroaryl ring is optionally linearly fused to a second 5-6 membered aryl or heteroaryl ring having 0-3 heteroatoms independently selected from N, O, or S;
    wherein said 3-7 membered monocyclic or 6-12 membered bicyclic saturated or partially unsaturated carbocyclic ring or said 3-7 membered monocyclic or a 6-12 membered bicyclic heterocyclic ring is optionally spirocyclic or linearly fused to a 4-7 membered saturated or partially unsaturated heterocyclic or carbocyclic ring;
      wherein said 4-7 membered saturated or partially unsaturated heterocyclic or carbocyclic fused ring contains 0-3 heteroatoms independently selected from N, $NR^3$, O, S, SO, or $SO_2$; and
  wherein $Ar^1$ is optionally substituted with 1-3 J groups.

As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito, 1999, and "March's Advanced Organic Chemistry", 5$^{th}$ Ed., Ed.: Smith, M. B. and March, J., Wiley & Sons, New York, 2001, the entire contents of which are hereby incorporated by reference.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group", as used herein, means a straight-chain or branched $C_1$-$C_8$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation, and includes aryl rings.

The term "aryl" used alone or as part of a larger moiety as in "aralkyl", "aralkoxy", or "aryloxyalkyl", refers to monocyclic, bicyclic and tricyclic ring systems, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems in which one or more ring members is a heteroatom, and wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "patient", as used herein, means an animal, preferably a mammal, and most preferably a human.

The term "treating" as used herein refers to the alleviation of symptoms of a particular disorder in a patient or the improvement of an ascertainable measurement associated with a particular disorder.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

According to one embodiment, Ring A of formula I is a 5-6 membered heteroaryl ring having 1-3 heteroatoms independently selected from N, O, or S;
  wherein said 5-6 membered heteroaryl ring system is optionally linearly fused to a second 5-6 membered aryl or heteroaryl ring;
  wherein said 5-6 membered aryl or heteroaryl fused ring contains 0-3 heteroatoms independently selected from N, O, or S; and
  wherein any of said rings is optionally substituted with up to 2 substituents independently selected from J.

According to another embodiment, Ring A of formula I is an optionally substituted ring selected from rings a, b, c, d, e, or f:

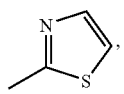
a

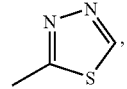
b

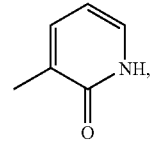
c

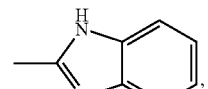
d

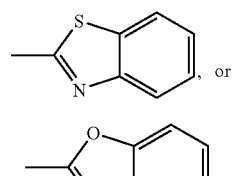
e

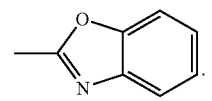
f

In some embodiments of formula I, L is —C(O)N(R$^4$) and R$^4$ is hydrogen.

In other embodiments of formula I, L is —N(R$^4$)C(O) and R$^4$ is hydrogen.

In yet other embodiments of formula I, L is a bond.

In another embodiment of compounds of formula I, R$^1$ is hydrogen.

In another embodiment of compounds of formula I, Ring A of formula I is a 5-6 membered heteroaryl ring having 1-3 heteroatoms independently selected from N, O, or S;
  wherein said 5-6 membered heteroaryl ring system is optionally linearly fused to a second 5-6 membered aryl or heteroaryl ring;
  wherein said 5-6 membered aryl or heteroaryl fused ring contains 0-3 heteroatoms independently selected from N, O, or S; and
  wherein any of said rings is optionally substituted with up to 2 substituents independently selected from J;
L is —C(O)N(R$^4$) and R$^4$ is hydrogen; and
R$^1$ is hydrogen.

In another embodiment of compounds of formula I, R$^1$ is OR$^5$, wherein R$^5$ is —(C$_1$-C$_4$)-straight or branched alkyl.

In other embodiments of compounds of formula I, R$^1$ is OR$^5$ wherein R$^5$ is methyl, ethyl or isopropyl.

In yet other embodiments of compounds of formula I, R$^1$ is OR$^5$, wherein R$^5$ is hydrogen.

In another embodiment of compounds of formula I, Q is a bond, t is 1, and R$^2$ is Ar$^1$.

In other embodiments of compounds of formula I, Q is —C(O)NR$^+$ wherein R$^+$ is hydrogen, t is 1, and R$^2$ is Ar$^1$ wherein Ar$^1$ is a 5-6 membered monocyclic or a 7-11 membered bicyclic aryl ring, a 5-6 membered heteroaryl ring having 1-4 heteroatoms independently selected from N, O, or S wherein said 5-6 membered heteroaryl ring is optionally linearly fused to a second 5-6 membered aryl or heteroaryl ring having 0-3 heteroatoms independently selected from N, O, or S and wherein Ar$^1$ is optionally substituted with 1-2 J groups.

In yet other embodiments of compounds of formula I, t is zero.

According to another embodiment, the present invention relates to compounds of formula II:

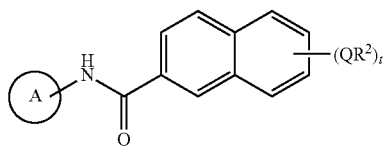

II or a pharmaceutically acceptable salt thereof, wherein Q, $R^2$, t, and Ring A are as defined above.

Other embodiments describing $R^2$, Q, t, and Ring A groups of formula II are those described for formula I above.

In some embodiments of compounds of formula II, Ring A is a 5-6 membered heteroaryl ring having 1-3 heteroatoms independently selected from N, O, or S;
wherein said 5-6 membered heteroaryl ring system is optionally linearly fused to a second 5-6 membered aryl or heteroaryl ring;
wherein said 5-6 membered aryl or heteroaryl fused ring contains 0-3 heteroatoms independently selected from N, O, or S; and
wherein any of said rings is optionally substituted with up to 2 substituents independently selected from J.

In other embodiments of compounds of formula II, Ring A is an optionally substituted ring selected from rings a, b, c, d, e, or f:

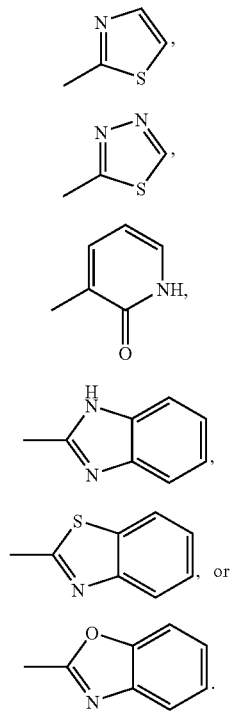

In other embodiments of compounds of formula II, Q is a bond, t is 1, and $R^2$ is $Ar^1$.

In yet other embodiments of compounds of formula II, Q is a bond, t is 1, and $R^2$ is $Ar^1$ and $Ar^1$ is a 5-6 membered monocyclic or a 7-11 membered bicyclic aryl ring, a 5-6 membered heteroaryl ring having 1-4 heteroatoms independently selected from N, O, or S wherein said 5-6 membered heteroaryl ring is optionally linearly fused to a second 5-6 membered aryl or heteroaryl ring having 0-3 heteroatoms independently selected from N, O, or S and wherein $Ar^1$ is optionally substituted with 1-2 J groups.

In another embodiment of compounds of formula II, Q is —C(O)$NR^+$ wherein $R^+$ is hydrogen, t is 1, and $R^2$ is $Ar^1$ wherein $Ar^1$ is a 5-6 membered monocyclic or a 7-11 membered bicyclic aryl ring, a 5-6 membered heteroaryl ring having 1-4 heteroatoms independently selected from N, O, or S wherein said 5-6 membered heteroaryl ring is optionally linearly fused to a second 5-6 membered aryl or heteroaryl ring having 0-3 heteroatoms independently selected from N, O, or S and wherein $Ar^1$ is optionally substituted with 1-2 J groups.

In yet other embodiments of compounds of formula II, t is zero.

In some embodiments of compounds of formula II, t is zero and Ring A is an optionally substituted ring selected from rings a, b, c, d, e, or f:

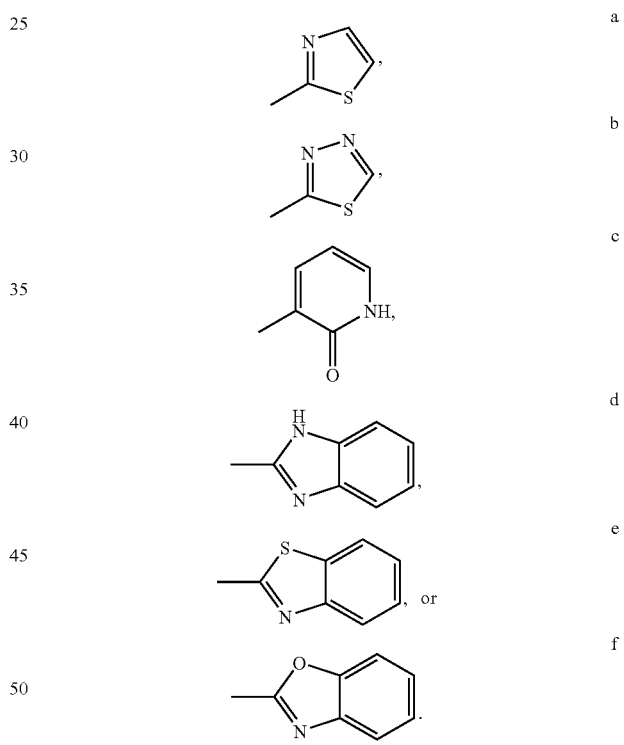

Examples of other suitable Ring A moieties include but are not limited to:

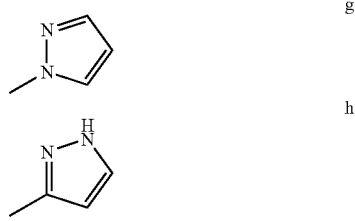

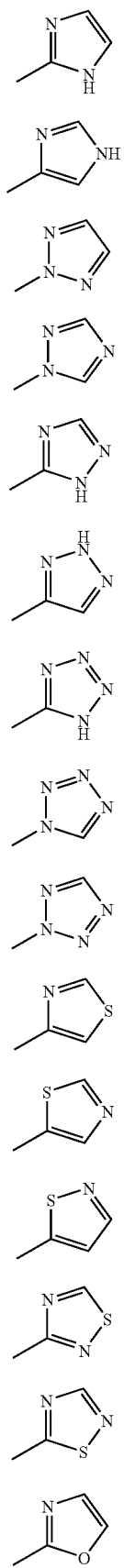
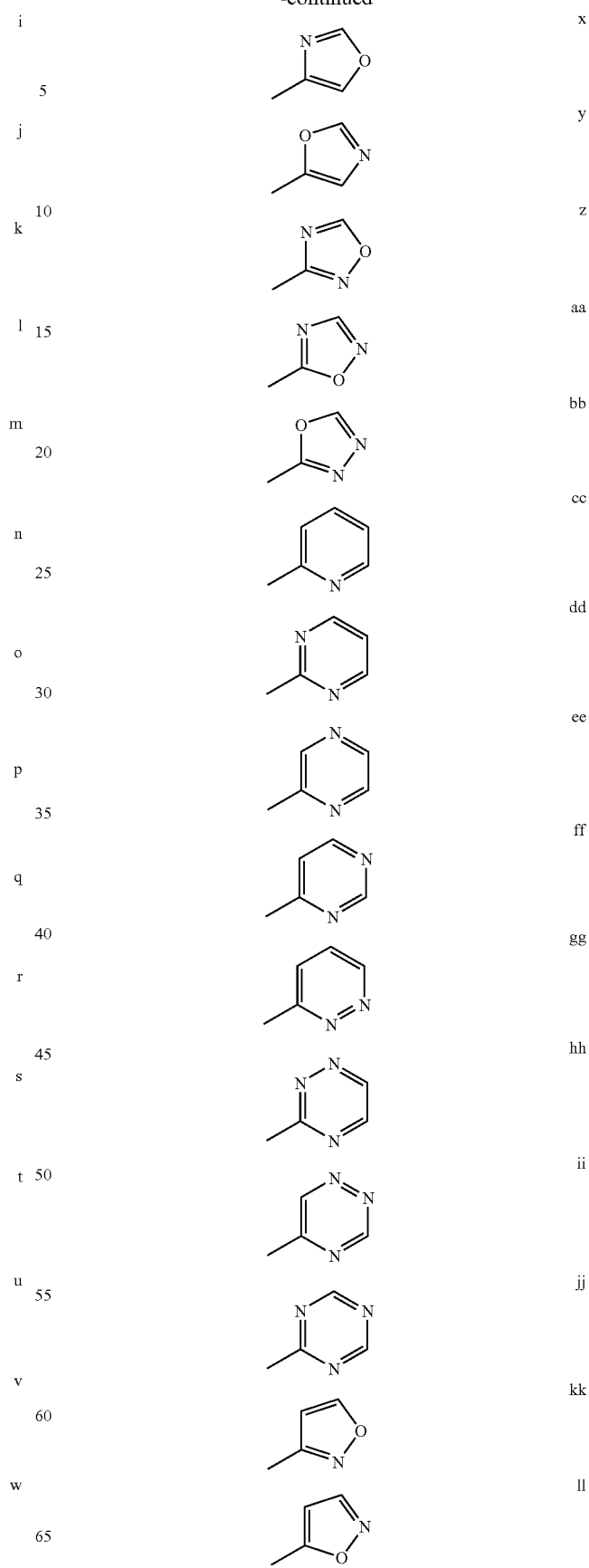

13

-continued

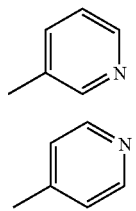

mm nn wherein each Ring A is optionally substituted as defined above.

A structural embodiment of formula I is compound 5 below:

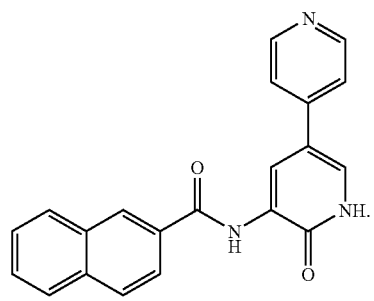

5

The compounds of this invention may be prepared in general by methods known to those skilled in the art for analogous compounds, as illustrated by the general Schemes I shown below and the Examples set forth infra. The compounds of formula I and starting materials useful for producing the compounds of formula I may be commercially available from chemical reagent supply companies such as Aldrich Chemical Co., Sigma Chemical Co. Compounds 5-12 were purchased from Specs (Wakefield, R. I.) and Chemical Diversity Labs, Inc. (San Diego, Calif.). Compounds can also be prepared by those of ordinary skill in the art following procedures set forth in references such as, "Fieser and Fieser's Reagents for Organic Synthesis", Volumes 1-15, John Wiley and Sons, 1991; "Rodd's Chemistry of Carbon Compounds", Volumes 1-5 and Supplements, Elsevier Science Publishers, 1989; and "Organic Reactions", Volumes 1-40, John Wiley and Sons, 1991.

Reagents and solvents and their abbreviations that may be useful for the preparation of compounds of formula I using general methods known to those skilled in the art include but are not limited to the following:

| | |
|---|---|
| THF | tetrahydrofuran |
| DMF | N,N,-dimethylformamide |
| EtOAc | ethyl acetate |
| CH$_2$Cl$_2$ | methylene chloride |
| DMSO | dimethyl sulfoxide |
| CH$_3$CN | acetonitrile |
| Et$_3$N | triethylamine |
| DIPEA | diisopropylethylamine |
| TFA | trifluoroacetic acid |
| DBU | 1,8-diazabicyclo[5.4.0]undec-7-ene |
| HOSu | N-hydroxysuccinimide |
| HOBt | 1-hydroxybenzotriazole hydrate |
| HOAt | 1-hydroxy-7-azabenzotriazole |
| EDC | 1-(3-dimethylaminopropyl)-3-ethylcarbodiimide hydrochloride |
| CDI | 1,1'-carbonyldiimidazole |

14

-continued

| | |
|---|---|
| DCC | 1,3-dicyclohexylcarbodiimide |
| PyBOP | tris(pyrrolidino)bromophosphonium hexafluorophosphate |
| 4-DMAP | 4-dimethylaminopyridine |
| K$_2$CO$_3$ | potassium carbonate |
| Na$_2$CO$_3$ | sodium carbonate |
| Li$_2$CO$_3$ | lithium carbonate |
| Cs$_2$CO$_3$ | cesium carbonate |
| NaHCO$_3$ | sodium bicarbonate |
| NaOH | sodium hydroxide |
| KOH | potassium hydroxide |
| LiOH | lithium hydroxide |
| MS | mass spectrometry |

Scheme I

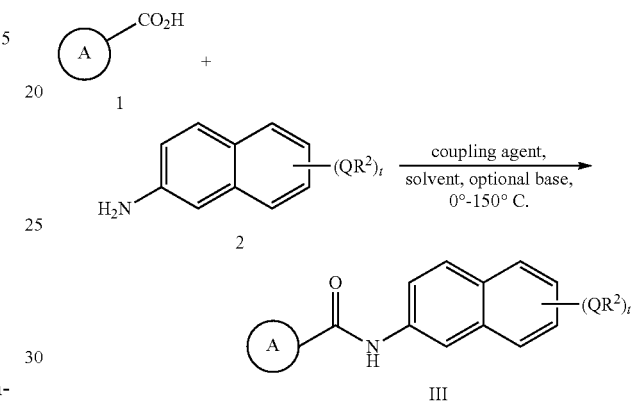

Scheme II

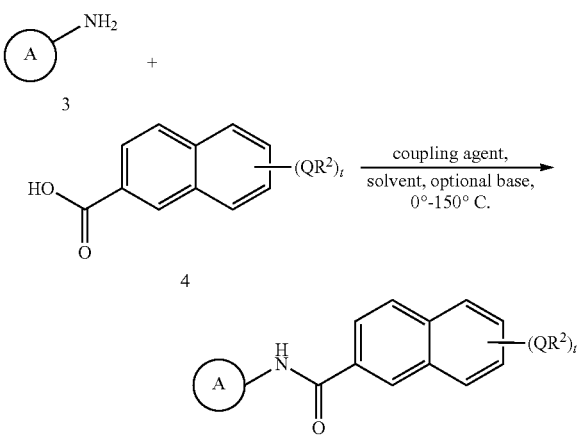

Schemes I and II above show general methods for preparing compounds of formula III and formula II of this invention wherein L and R$^4$ are as shown [either —C(O)NH in Scheme I or —NHC(O) in Scheme II]. Therein, an optionally substituted heteroarylamine 3 or naphthylamine 2 of interest (either purchased commercially or prepared according to methods known to one of skill in the art) is mixed with an optionally substituted naphthoic acid 4 or an optionally substituted heteroarylcarboxylic acid 1 of interest (either purchased commercially or prepared according to methods known to one of skill in the art and wherein Q, R$^2$, and t are as defined in any of the embodiments described herein) in a suitable solvent and with a suitable coupling agent, with or without a suitable base and the mixture is stirred under a suitable atmosphere, at a suitable temperature and for a suitable time to give, after isolation and purification, if necessary, compounds of formulas I, II or III as oils, foams, lyophilates, solids, or crystalline solids. Suitable solvents include but are not limited to $CH_2Cl_2$, DMF, DMSO, $CH_3CN$, EtOAc, THF, benzene, etc., or mixtures thereof. Suitable coupling agents include, but are not limited to EDC, CDI, DCC, HOAt, HOSu, HOBt, PyBOP, etc., or mixtures thereof. Suitable temperatures include, but are not limited to 0° C. to 150° C. Suitable bases include, but are not limited to DIPEA, $Et_3N$, pyridine, 4-DMAP, $K_2CO_3$, $Na_2CO_3$, $Li_2CO_3$, $Cs_2CO_3$, $NaHCO_3$, NaOH, KOH, LiOH etc., or mixtures thereof. Suitable atmospheres include but are not limited to air, nitrogen, argon, or mixtures thereof. Suitable times include but are not limited to 10 minutes to 48 hours.

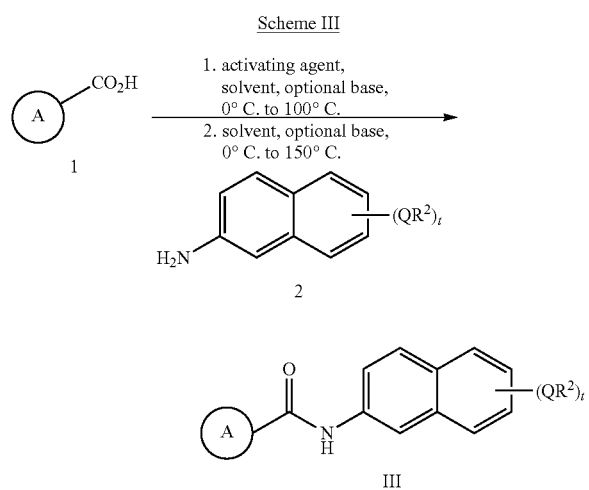

Scheme III

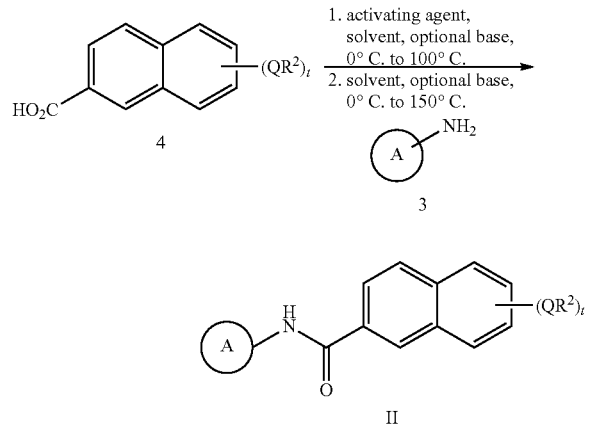

Scheme IV

Schemes III and IV above, show other general methods for preparing compounds of formula III and formula II of this invention wherein L and $R^4$ are as shown. Therein, an optionally substituted naphthoic acid 4 or an optionally substituted heteroarylcarboxylic acid 1 of interest (either purchased commercially or prepared according to methods known to one of skill in the art) is mixed with a suitable activating agent in a suitable solvent with or without a suitable base and stirred for a suitable time at a suitable temperature and under a suitable atmosphere. Suitable activating agents to prepare activated intermediates (e.g., mixed anhydrides, acid chlorides, etc.) include but are not limited to CDI, HOSu, —($C_1$-$C_6$) straight or branched alkyl chloroformates or aryl chloroformates, and oxalyl chloride. Suitable solvents include but are not limited to $CH_2Cl_2$, DMF, DMSO, $CH_3CN$, EtOAc, THF, benzene, etc., or mixtures thereof. Suitable temperatures include, but are not limited to 0° C. to 150° C. Suitable bases include, but are not limited to DIPEA, $Et_3N$, pyridine, 4-DMAP, $K_2CO_3$, NaOH, etc., or mixtures thereof. Suitable atmospheres include but are not limited to air, nitrogen, argon or mixtures thereof. Suitable times include but are not limited to 10 minutes to 48 hours.

Activated intermediates may optionally be isolated or used directly as is and is thereafter treated with stirring, either dropwise or all at once, with an optionally substituted heteroarylamine 3 or naphthyl amine 2 of interest (either purchased commercially or prepared according to methods known to one of skill in the art and wherein Q, $R^2$, and t are as defined in any of the embodiments described herein) in a suitable solvent, with a suitable base, if necessary, and at a suitable temperature under a suitable atmosphere and for a suitable time to give, after isolation and purification, if necessary, compounds of formula I, II or III as oils, foams, lyophilates, solids, or crystalline solids. Suitable solvents include but are not limited to $CH_2Cl_2$, DMF, DMSO, $CH_3CN$, EtOAc, THF, benzene, etc., or mixtures thereof. Suitable temperatures include, but are not limited to 0° C. to 150° C. Suitable bases include, but are not limited to DIPEA, $Et_3N$, pyridine, 4-DMAP, $K_2CO_3$, NaOH, etc., or mixtures thereof. Suitable atmospheres include but are not limited to air, nitrogen, argon or mixtures thereof. Suitable times include but are not limited to 10 minutes to 48 hours.

One of skill in the art would recognize that a variety of compounds of the present invention may be prepared according to the general method of Schemes I and II methods known in the art, and the synthetic Examples set forth below.

The compounds of this invention are inhibitors of bacterial IMPDH as determined by enzymatic assay. The activity of a compound utilized in this invention as an inhibitor of IMPDH may be assayed in vitro according to methods known in the art. The details of the conditions used for the enzymatic assay and the conditions that may be used for an antimicrobial susceptibility assay are set forth in the Examples below.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit IMPDH, or to measurably decrease bacterial quantity, in a biological sample or in a patient. Preferably the composition of this invention is formulated for administration to a patient in need of such composition. Most preferably, the composition of this invention is formulated for oral administration to a patient.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "patient", as used herein, means an animal, preferably a mammal, and most preferably a human.

The term "detectably inhibit", as used herein means a measurable change in IMPDH activity between a sample comprising said composition and IMPDH and an equivalent sample comprising IMPDH in the absence of said composition.

As used herein, the term "measurably decrease bacterial quantity", as used herein means a measurable change in the number of bacteria between a sample containing said composition and a sample containing only bacteria.

A "pharmaceutically acceptable salt" means any non-toxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of IMPDH.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$ ($C_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus faecalis, Enterococcus faecium, Klebsiella pneumoniae, Enterobacter* sps. *Proteus* sps. *Pseudomonas aeruginosa, E. coli, Serratia marcesens, Staphylococcus aureus,* Coag. Neg. Staph, *Haemophilus influenzae, Bacillus anthracis, Mycoplasma pneumoniae, Moraxella catarralis, Chlamydia pneumoniae, Legionella pneumophila, Mycobacterium tuberculosis, Staphylococcus epidermidis,* or *Helicobacter pylori.*

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of resistant bacterial infections caused by bacteria such as Methicillin resistant *Staphylococcus aureus,* Fluoroquinolone resistant *Staphylococcus aureus,* Vancomycin intermediate resistant *Staphylococcus aureus,* Linezolid resistant *Staphylococcus aureus,* Penicillin resistant *Streptococcus pneumoniae,* Macrolide resistant *Streptococcus pneumoniae,* Fluoroquinolone resistant *Streptococcus pneumoniae,* Vancomycin resistant *Enterococcus faecalis,* Linezolid resistant *Enterococcus faecalis,* Fluoroquinolone resistant *Enterococcus faecalis,* Vancomycin resistant *Enterococcus faecaium,* Linezolid resistant *Enterococcus faecaium,* Fluoroquinolone resistant *Enterococcus faecaium,* Ampicillin resistant *Enterococcus faecaium,* Macrolide resistant *Haemophilus influenzae,* β-lactam resistant *Haemophilus influenzae,* Fluoroquinolone resistant *Haemophilus influenzae,* β-lactam resistant *Moraxella catarrhalis,* Methicillin resistant *Staphylococcus epidermidis,* Methicillin resistant *Staphylococcus epidermidis,* Vancomycin resistant *Staphylococcus epidermidis,* Fluoroquinolone resistant *Staphylococcus epidermidis,* Macrolide resistant *Mycoplama pneumoniae,* Isoniazid resistant *Mycobacterium tuberculosis,* Rifampin resistant *Mycobacterium tuberculosis,* Methicillin resistent Coagulase negative staphylcocci, Fluoroquinolone resistant Coagulase negative staphylcocci, Glycopeptide intermediate resistant *Staphylococcus aureus,* Vancomycin resistant *Staphylococcus aureus,* Hetero vancomycin intermediate resistant *Staphylococcus aureus,* Hetero vancomycin resistant *Staphylococcus aureus,* Macrolide-Lincosamide-Streptogramin resistant *Staphylococcus,* β-lactam resistant *Enterococcus faecalis,* β-lactam resistant *Enterococcus faecium,* Ketolide resistant *Streptococcus pneumoniae,* Ketolide resistant *Streptococcus pyogenes,* Macrolide resistant *Streptococcus pyogenes,* or Vancomycin resistant *staphylococcus epidermidis.*

Typically, the pharmaceutical compositions of this invention will be administered from about 1 to 5 times per day or alternatively, as a continuous infusion. Or, alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated". Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, or an agent which increases the susceptibility of bacterial organisms to antibiotics.

According to another embodiment, the present invention provides a pharmaceutical composition comprising a compound of formula I, and a pharmaceutically acceptable carrier, adjuvant, or vehicle.

In another embodiment of the pharmaceutical compositions of this invention, Ring A is a 5-6 membered heteroaryl ring having 1-3 heteroatoms independently selected from N, O, or S;
  wherein said 5-6 membered heteroaryl ring system is optionally linearly fused to a second 5-6 membered aryl or heteroaryl ring;
  wherein said 5-6 membered aryl or heteroaryl fused ring contains 0-3 heteroatoms independently selected from N, O, or S; and
  wherein any of said rings is optionally substituted with up to 2 substituents independently selected from J.

In another embodiment of the pharmaceutical compositions of this invention, L is —C(O)N($R^4$) and $R^4$ is hydrogen. In yet another embodiment, L is —N($R^4$)C(O) and $R^4$ is hydrogen.

In another embodiment of the pharmaceutical compositions of this invention, $R^1$ is hydrogen. In yet another embodiment, $R^1$ is $OR^5$ and $R^5$ is —($C_1$-$C_4$)-straight or branched alkyl. In another embodiment, $R^5$ is methyl, ethyl or isopropyl. In yet another embodiment, $R^1$ is $OR^5$ and $R^5$ is hydrogen.

In another embodiment of the pharmaceutical compositions of this invention, Q is a bond, t is 1, and $R^2$ is $Ar^1$. In yet another embodiment, Q is —C(O)$NR^+$ wherein $R^+$ is hydrogen, t is 1, and $R^2$ is $Ar^1$ wherein $Ar^1$ is a 5-6 membered monocyclic or a 7-11 membered bicyclic aryl ring, a 5-6 membered heteroaryl ring having 1-4 heteroatoms independently selected from N, O, or S wherein said 5-6 membered heteroaryl ring is optionally linearly fused to a second 5-6 membered aryl or heteroaryl ring having 0-3 heteroatoms independently selected from N, O, or S and wherein $Ar^1$ is optionally substituted with 1-2 J groups.

In another embodiment of the pharmaceutical compositions of this invention, t is zero.

According to another embodiment, the present invention provides a pharmaceutical composition comprising a compound of formula I that additionally comprises one or more additional therapeutic agents selected from an antibiotic or an agent which increases the susceptibility of bacterial organisms to antibiotics.

Agents which increase the susceptibility of bacterial organisms to antibiotics are known. For example, U.S. Pat. Nos. 5,523,288, 5,783,561 and 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in *Microbiological Reviews* (1992) pp. 395-411, and the sensitization of gram-negative bacteria has been described by Tsubery, H., et al, in *J Med. Chem.* (2000) pp. 3085-3092.

According to another embodiment, the present invention provides a method of inhibiting an IMPDH-mediated function in a patient comprising the step of administering to said patient a pharmaceutical composition comprising a compound of formula I. In another embodiment, said patient is a human.

According to another embodiment, the present invention provides a method of inhibiting bacterial IMPDH in a patient, comprising administering to said patient a therapeutically effective amount of a compound of formula I:

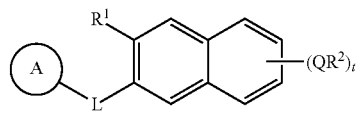

I or a pharmaceutically acceptable salt thereof, wherein:
Ring A is a 5-6 membered heteroaryl ring or a 4-7 membered saturated or partially unsaturated heterocyclic ring each ring having 1-4 heteroatoms independently selected from N, $NR^3$, O, S, SO, or $SO_2$;
  wherein said 5-6 membered heteroaryl ring system is optionally linearly fused to a second 5-6 membered aryl or heteroaryl ring or optionally linearly fused to a 4-7 membered saturated or partially unsaturated heterocyclic or carbocyclic ring;
    wherein said 5-6 membered aryl or heteroaryl fused ring contains 0-3 heteroatoms independently selected from N, O, or S;
    wherein said 4-7 membered fused ring contains 0-3 heteroatoms independently selected from N, $NR^3$, O, S, SO, or $SO_2$;
  wherein said 4-7 membered saturated or partially unsaturated heterocyclic ring is optionally linearly fused to a second 5-6 membered aryl or heteroaryl ring or optionally spirocyclic bound to a 4-7 membered saturated or partially unsaturated heterocyclic or carbocyclic ring;
    wherein said 5-6 membered aryl or heteroaryl fused ring contains 0-3 heteroatoms independently selected from N, O, or S;
    wherein said 4-7 membered spirocyclic ring contains 0-3 heteroatoms independently selected from N, $NR^3$, O, S, SO, or $SO_2$; and
  wherein any of said rings is optionally substituted with up to 2 substituents independently selected from J;
    J is —($C_1$-$C_4$)-straight or branched alkyl chain, —($C_2$-$C_4$)-straight or branched alkenyl or alkynyl, halogen, -(T)$_y$-Ar, -(T)$_y$-R', —$CF_3$, —$OCF_3$, oxo, —C(O)R', —C(O)C(O)R', —$CO_2$R', —OR', —N(R')$_2$, —SR', —$NO_2$, —CN, —C(O)N(R')$_2$, —OC(O)N(R')$_2$, —NR'C(O)R', —NR'C(O)N(R')$_2$, —N(OR')R', —C(=NOR')R', —$SO_2$R', —$SO_2$N(R')$_2$, —NR'$SO_2$R', —P(O)R')$_2$, —P(O)(OR')$_2$, or —OP(O)(OR')$_2$; wherein
      y is 0 or 1;
      T is a ($C_1$-$C_4$)-straight or branched alkyl chain, wherein one methylene unit of T is optionally replaced by —O—, —C(O)—, —NH—, or —S—;
      each R' is independently selected from hydrogen, a ($C_1$-$C_4$)-straight or branched alkyl chain, or a 5-6 membered saturated, unsaturated, or aryl ring having 0-3 heteroatoms independently selected from N, O, or S; or
      two R' groups together with the nitrogen to which they are bound optionally form a 3-6 membered heterocyclic ring; and
      each R' is substituted with 0-3 groups independently selected from halogen, oxo, $R^0$, N($R^0$)$_2$, $OR^0$, $CO_2R^0$, $NR^0C(O)R^0$, C(O)N($R^0$)$_2$, $SO_2R^0$, $SO_2$N($R^0$)$_2$, or $NR^0SO_2R^0$; wherein
        each $R^0$ is independently selected from hydrogen, a ($C_1$-$C_4$)-straight or branched alkyl chain, or a 5-6 membered saturated, unsaturated, or aryl ring having 0-3 heteroatoms independently selected from N, O, or S;

two substituents on adjacent positions of any ring may be taken together to form a 5-7 membered saturated, partially unsaturated, heterocyclic or carbocyclic ring or 5-6 membered aryl or heteroaryl ring, each ring having 0-3 heteroatoms independently selected from N, O, or S; Ar is a 3-8 membered saturated or unsaturated carbocyclic ring, a 5-6 membered aryl ring, a 3-7 membered heterocyclic ring having 1-3 heteroatoms independently selected from N, NR³, O, S, SO, or SO₂, or a 5-6 membered heteroaryl ring having 1-4 heteroatoms independently selected from N, O, or S, wherein:
Ar is optionally substituted with 1-3 J groups; and
R³ is hydrogen, —(C₁-C₄)-straight or branched alkyl, —(C₂-C₄)-straight or branched alkenyl or alkynyl, -(T)$_y$-Ar, C(O)R', CO₂R', OR', N(R')₂, C(O)N(R')₂, NR'C(O)R', SO₂R', SO₂N(R')₂, or NR'SO₂R';
L is —C(O)N(R⁴), —N(R⁴)C(O), or a bond; wherein
R⁴ is selected from hydrogen or —(C₁-C₃)-straight or branched alkyl;
R¹ is selected from hydrogen, halogen, OR⁵, or N(R⁵)₂; wherein
each R⁵ is independently hydrogen, —(C₁-C₄)-straight or branched alkyl, —(C₂-C₄)-straight or branched alkenyl or alkynyl, or C(O)R';
Q is a bond or a —(C₁-C₃)-straight or branched alkyl chain wherein one methylene unit of Q is optionally replaced by —NR⁺—, —S—, —O—, —C(S)—, —CO₂—, —OC(O)—, —C(O)—, —C(O)C(O)—, —C(O)NR⁺—, —NR⁺C(O)—, —NR⁺CO₂—, —SO₂NR⁺—, —NR⁺SO₂—, —C(O)NR⁺NR⁺—, —NR⁺C(O)NR⁺—, —OC(O)NR⁺—, —NR⁺NR⁺—, —NR⁺SO₂NR⁺—, —S(O)—, —SO₂—, —P(O)—, —PO₂—, or —P(O)R⁺—;
wherein R⁺ is independently hydrogen, —(C₁-C₄)-straight or branched alkyl, or —(C₂-C₄)—straight or branched alkenyl or alkynyl optionally substituted with 1-3 groups independently selected from halogen, oxo, R⁰, N(R⁰)₂, OR⁰, CO₂R⁰, NR⁰C(O)R⁰, C(O)N(R⁰)₂, SO₂R⁰, SO₂N(R⁰)₂, or NR⁰SO₂R⁰;
t is 0-2; and
R² is hydrogen, —(C₁-C₃)-straight or branched alkyl, —(C₂-C₄)-straight or branched alkenyl or alkynyl, halogen, NO₂, CF₃, CN, or Ar¹;
wherein Ar¹ is a 3-7 membered monocyclic or a 6-12 membered bicyclic saturated or partially unsaturated carbocyclic ring, a 5-6 membered monocyclic or a 7-11 membered bicyclic aryl ring, a 3-7 membered monocyclic or a 6-12 membered bicyclic heterocyclic ring having 1-5 heteroatoms independently selected from N, NR³, O, S, SO, or SO₂, or a 5-6 membered heteroaryl ring having 1-4 heteroatoms independently selected from N, O, or S;
wherein said 5-6 membered monocyclic or 7-11 membered bicyclic aryl ring or 5-6 membered heteroaryl ring is optionally linearly fused to a second 5-6 membered aryl or heteroaryl ring having 0-3 heteroatoms independently selected from N, O, or S;
wherein said 3-7 membered monocyclic or 6-12 membered bicyclic saturated or partially unsaturated carbocyclic ring or said 3-7 membered monocyclic or a 6-12 membered bicyclic heterocyclic ring is optionally spirocyclic or linearly fused to a 4-7 membered saturated or partially unsaturated heterocyclic or carbocyclic ring;
wherein said 4-7 membered saturated or partially unsaturated heterocyclic or carbocyclic fused ring contains 0-3 heteroatoms independently selected from N, NR³, O, S, SO, or SO₂; and
wherein Ar¹ is optionally substituted with 1-3 J groups.

According to another embodiment, said patient is a human.

According to another embodiment, the present invention provides a method of inhibiting bacterial IMPDH to treat or lessen the severity of a bacterial infection in a patient, comprising administering to said patient a therapeutically effective amount of a compound of formula I:

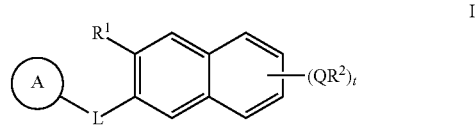

or a pharmaceutically acceptable salt thereof, wherein:
Ring A is a 5-6 membered heteroaryl ring or a 4-7 membered saturated or partially unsaturated heterocyclic ring each ring having 1-4 heteroatoms independently selected from N, NR³, O, S, SO, or SO₂;
wherein said 5-6 membered heteroaryl ring system is optionally linearly fused to a second 5-6 membered aryl or heteroaryl ring or optionally linearly fused to a 4-7 membered saturated or partially unsaturated heterocyclic or carbocyclic ring;
wherein said 5-6 membered aryl or heteroaryl fused ring contains 0-3 heteroatoms independently selected from N, O, or S;
wherein said 4-7 membered fused ring contains 0-3 heteroatoms independently selected from N, NR³, O, S, SO, or SO₂;
wherein said 4-7 membered saturated or partially unsaturated heterocyclic ring is optionally linearly fused to a second 5-6 membered aryl or heteroaryl ring or optionally spirocyclic bound to a 4-7 membered saturated or partially unsaturated heterocyclic or carbocyclic ring;
wherein said 5-6 membered aryl or heteroaryl fused ring contains 0-3 heteroatoms independently selected from N, O, or S;
wherein said 4-7 membered spirocyclic ring contains 0-3 heteroatoms independently selected from N, NR³, O, S, SO, or SO₂; and
wherein any of said rings is optionally substituted with up to 2 substituents independently selected from J;
J is —(C₁-C₄)-straight or branched alkyl chain, —(C₂-C₄)-straight or branched alkenyl or alkynyl, halogen, -(T)$_y$-Ar, -(T)$_y$-R', —CF₃, —OCF₃, oxo, —C(O)R', —C(O)C(O)R', —CO₂R', —OR', —N(R')₂, —SR', —NO₂, —CN, —C(O)N(R')₂, —OC(O)N(R')₂, —NR'C(O)R', —NR'C(O)N(R')₂, —N(OR')R', —C(=NOR')R', —SO₂R', —SO₂N(R')₂, —NR'SO₂R', —P(O)R'₂, —P(O)(OR')₂, or —OP(O)(OR')₂; wherein
y is 0 or 1;
T is a (C₁-C₄)-straight or branched alkyl chain, wherein one methylene unit of T is optionally replaced by —O—, —C(O)—, —NH—, or —S—;
each R' is independently selected from hydrogen, a (C₁-C₄)-straight or branched alkyl chain, or a 5-6 membered saturated, unsaturated, or aryl ring having 0-3 heteroatoms independently selected from N, O, or S; or two R' groups together with the nitrogen to which they are bound optionally form a 3-6 membered heterocyclic ring; and each R' is substituted with 0-3 groups independently selected from halogen, oxo, $R^0$, $N(R^0)_2$, $OR^0$, $CO_2R^0$, $NR^0C(O)R^0$, $C(O)N(R^0)_2$, $SO_2R^0$, $SO_2N(R^0)_2$, or $NR^0SO_2R^0$; wherein each $R^0$ is independently selected from hydrogen, a $(C_1-C_4)$—straight or branched alkyl chain, or a 5-6 membered saturated, unsaturated, or aryl ring having 0-3 heteroatoms independently selected from N, O, or S;

two substituents on adjacent positions of any ring may be taken together to form a 5-7 membered saturated, partially unsaturated, heterocyclic or carbocyclic ring or 5-6 membered aryl or heteroaryl ring, each ring having 0-3 heteroatoms independently selected from N, O, or S;

Ar is a 3-8 membered saturated or unsaturated carbocyclic ring, a 5-6 membered aryl ring, a 3-7 membered heterocyclic ring having 1-3 heteroatoms independently selected from N, $NR^3$, O, S, SO, or $SO_{02}$, or a 5-6 membered heteroaryl ring having 1-4 heteroatoms independently selected from N, O, or S, wherein:

Ar is optionally substituted with 1-3 J groups; and $R^3$ is hydrogen, $-(C_1-C_4)$-straight or branched alkyl, $-(C_2-C_4)$-straight or branched alkenyl or alkynyl, $-(T)_y$-Ar, $C(O)R'$, $CO_2R'$, $OR'$, $N(R')_2$, $C(O)N(R')_2$, $NR'C(O)R'$, $SO_2R'$, $SO_2N(R')_2$, or $NR'SO_2R'$;

L is $-C(O)N(R^4)$, $-N(R^4)C(O)$, or a bond; wherein
$R^4$ is selected from hydrogen or $-(C_1-C_3)$-straight or branched alkyl;

$R^1$ is selected from hydrogen, halogen, $OR^5$, or $N(R^5)_2$; wherein
each $R^5$ is independently hydrogen, $-(C_1-C_4)$-straight or branched alkyl, $-(C_2-C_4)$-straight or branched alkenyl or alkynyl, or $C(O)R'$;

Q is a bond or a $-(C_1-C_3)$-straight or branched alkyl chain wherein one methylene unit of Q is optionally replaced by $-NR^+-$, $-S-$, $-O-$, $-C(S)-$, $-CO_2-$, $-OC(O)-$, $-C(O)-$, $-C(O)C(O)-$, $-C(O)NR^+-$, $-NR^+C(O)-$, $-NR^+CO_2-$, $-SO_2NR^+-$, $-NR^+SO_2-$, $-C(O)NR^+NR^+-$, $-NR^+C(O)NR^+-$, $-OC(O)NR^+-$, $-NR^+NR^+-$, $-NR^+SO_2NR^+-$, $-S(O)-$, $-SO_2-$, $-P(O)-$, $-PO_2-$, or $-P(O)R^+-$;

wherein $R^+$ is independently hydrogen, $-(C_1-C_4)$-straight or branched alkyl, or $-(C_2-C_4)$-straight or branched alkenyl or alkynyl optionally substituted with 1-3 groups independently selected from halogen, oxo, $R^0$, $N(R^0)_2$, $OR^0$, $CO_2R^0$, $NR^0C(O)R^0$, $C(O)N(R^0)_2$, $SO_2R^0$, $SO_2N(R^0)_2$, or $NR^0SO_2R^0$;

t is 0-2; and $R^2$ is hydrogen, $-(C_1-C_3)$-straight or branched alkyl, $-(C_2-C_4)$-straight or branched alkenyl or alkynyl, halogen, $NO_2$, $CF_3$, CN, or $Ar^1$;

wherein $Ar^1$ is a 3-7 membered monocyclic or a 6-12 membered bicyclic saturated or partially unsaturated carbocyclic ring, a 5-6 membered monocyclic or a 7-11 membered bicyclic aryl ring, a 3-7 membered monocyclic or a 6-12 membered bicyclic heterocyclic ring having 1-5 heteroatoms independently selected from N, $NR^3$, O, S, SO, or $SO_2$, or a 5-6 membered heteroaryl ring having 1-4 heteroatoms independently selected from N, O, or S;

wherein said 5-6 membered monocyclic or 7-11 membered bicyclic aryl ring or 5-6 membered heteroaryl ring is optionally linearly fused to a second 5-6 membered aryl or heteroaryl ring having 0-3 heteroatoms independently selected from N, O, or S;

wherein said 3-7 membered monocyclic or 6-12 membered bicyclic saturated or partially unsaturated carbocyclic ring or said 3-7 membered monocyclic or a 6-12 membered bicyclic heterocyclic ring is optionally spirocyclic or linearly fused to a 4-7 membered saturated or partially unsaturated heterocyclic or carbocyclic ring;

wherein said 4-7 membered saturated or partially unsaturated heterocyclic or carbocyclic fused ring contains 0-3 heteroatoms independently selected from N, $NR^3$, O, S, SO, or $SO_2$; and wherein $Ar^1$ is optionally substituted with 1-3 J groups.

According to another embodiment, said patient is a human.

According to another embodiment, the present invention provides a method of inhibiting bacterial IMPDH, comprising contacting bacteria with a compound of formula I:

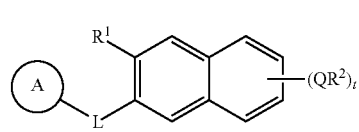

or a pharmaceutically acceptable salt thereof, wherein:

Ring A is a 5-6 membered heteroaryl ring or a 4-7 membered saturated or partially unsaturated heterocyclic ring each ring having 1-4 heteroatoms independently selected from N, $NR^3$, O, S, SO, or $SO_2$;

wherein said 5-6 membered heteroaryl ring system is optionally linearly fused to a second 5-6 membered aryl or heteroaryl ring or optionally linearly fused to a 4-7 membered saturated or partially unsaturated heterocyclic or carbocyclic ring;

wherein said 5-6 membered aryl or heteroaryl fused ring contains 0-3 heteroatoms independently selected from N, O, or S;

wherein said 4-7 membered fused ring contains 0-3 heteroatoms independently selected from N, $NR^3$, O, S, SO, or $SO_2$;

wherein said 4-7 membered saturated or partially unsaturated heterocyclic ring is optionally linearly fused to a second 5-6 membered aryl or heteroaryl ring or optionally spirocyclic bound to a 4-7 membered saturated or partially unsaturated heterocyclic or carbocyclic ring;

wherein said 5-6 membered aryl or heteroaryl fused ring contains 0-3 heteroatoms independently selected from N, O, or S;

wherein said 4-7 membered spirocyclic ring contains 0-3 heteroatoms independently selected from N, $NR^3$, O, S, SO, or $SO_2$; and wherein any of said rings is optionally substituted with up to 2 substituents independently selected from J;

J is $-(C_1-C_4)$-straight or branched alkyl chain, $-(C_2-C_4)$-straight or branched alkenyl or alkynyl, halogen, $-(T)_y$-Ar, $-(T)_y$-R', $-CF_3$, $-OCF_3$, oxo, $-C(O)R'$, $-C(O)C(O)R'$, $-CO_2R'$, $-OR'$, $-N(R')_2$, $-SR'$, $-NO_2$, $-CN$, $-C(O)N(R')_2$, $-OC(O)N(R')_2$, $-NR'C(O)R'$, $-NR'C(O)N(R')_2$, $-N(OR')R'$, $-C(=NOR')R'$, $-SO_2R'$, $-SO_2N(R')_2$, $-NR'SO_2R'$, $-P(O)R'_2$, $-P(O)(OR')_2$, or $-OP(O)(OR')_2$; wherein y is 0 or 1;

T is a ($C_1$-$C_4$)-straight or branched alkyl chain, wherein one methylene unit of T is optionally replaced by —O—, —C(O)—, —NH—, or —S—;

each R' is independently selected from hydrogen, a ($C_1$-$C_4$)-straight or branched alkyl chain, or a 5-6 membered saturated, unsaturated, or aryl ring having 0-3 heteroatoms independently selected from N, O, or S; or two R' groups together with the nitrogen to which they are bound optionally form a 3-6 membered heterocyclic ring; and each R' is substituted with 0-3 groups independently selected from halogen, oxo, $R^0$, $N(R^0)_2$, $OR^0$, $CO_2R^0$, $NR^0C(O)R^0$, $C(O)N(R^0)_2$, $SO_2R^0$, $SO_2N(R^0)_2$, or $NR^0SO_2R^0$; wherein each $R^0$ is independently selected from hydrogen, a ($C_1$-$C_4$)—straight or branched alkyl chain, or a 5-6 membered saturated, unsaturated, or aryl ring having 0-3 heteroatoms independently selected from N, O, or S;

two substituents on adjacent positions of any ring may be taken together to form a 5-7 membered saturated, partially unsaturated, heterocyclic or carbocyclic ring or 5-6 membered aryl or heteroaryl ring, each ring having 0-3 heteroatoms independently selected from N, O, or S;

Ar is a 3-8 membered saturated or unsaturated carbocyclic ring, a 5-6 membered aryl ring, a 3-7 membered heterocyclic ring having 1-3 heteroatoms independently selected from N, $NR^3$, O, S, SO, or $SO_2$, or a 5-6 membered heteroaryl ring having 1-4 heteroatoms independently selected from N, O, or S, wherein:

Ar is optionally substituted with 1-3 J groups; and $R^3$ is hydrogen, —($C_1$-$C_4$)-straight or branched alkyl, —($C_2$-$C_4$)-straight or branched alkenyl or alkynyl, -(T)$_y$-Ar, C(O)R', $CO_2R'$, OR', $N(R')_2$, $C(O)N(R')_2$, NR'C(O)R', $SO_2R'$, $SO_2N(R')_2$, or $NR'SO_2R'$;

L is —$C(O)N(R^4)$, —$N(R^4)C(O)$, or a bond; wherein $R^4$ is selected from hydrogen or —($C_1$-$C_3$)-straight or branched alkyl;

R' is selected from hydrogen, halogen, $OR^5$, or $N(R^5)_2$; wherein each $R^5$ is independently hydrogen, —($C_1$-$C_4$)-straight or branched alkyl, —($C_2$-$C_4$)-straight or branched alkenyl or alkynyl, or C(O)R';

Q is a bond or a —($C_1$-$C_3$)-straight or branched alkyl chain wherein one methylene unit of Q is optionally replaced by —$NR^+$—, —S—, —O—, —C(S)—, —$CO_2$—, —OC(O)—, —C(O)—, —C(O)C(O)—, —$C(O)NR^+$—, —$NR^+C(O)$—, —$NR^+CO_2$—, —$SO_2NR^+$—, —$NR^+SO_2$—, —$C(O)NR^+NR^+$—, —$NR^+C(O)NR^+$—, —$OC(O)NR^+$—, —$NR^+NR^+$—, —$NR^+SO_2NR^+$—S(O)—, —$SO_2$—, —P(O)—, —$PO_2$—, or —$P(O)R^+$—;

wherein $R^+$ is independently hydrogen, —($C_1$-$C_4$)-straight or branched alkyl, or —($C_2$-$C_4$)-straight or branched alkenyl or alkynyl optionally substituted with 1-3 groups independently selected from halogen, oxo, $R^0$, $N(R^0)_2$, $OR^0$, $CO_2R^0$, $NR^0C(O)R^0$, $C(O)N(R^0)_2$, $SO_2R^0$, $SO_2N(R^0)_2$, or $NR^0SO_2R^0$;

t is 0-2; and $R^2$ is hydrogen, —($C_1$-$C_3$)-straight or branched alkyl, —($C_2$-$C_4$)-straight or branched alkenyl or alkynyl, halogen, $NO_2$, $CF_3$, CN, or $Ar^1$;

wherein $Ar^1$ is a 3-7 membered monocyclic or a 6-12 membered bicyclic saturated or partially unsaturated carbocyclic ring, a 5-6 membered monocyclic or a 7-11 membered bicyclic aryl ring, a 3-7 membered monocyclic or a 6-12 membered bicyclic heterocyclic ring having 1-5 heteroatoms independently selected from N, $NR^3$, O, S, SO, or $SO_2$, or a 5-6 membered heteroaryl ring having 1-4 heteroatoms independently selected from N, O, or S;

wherein said 5-6 membered monocyclic or 7-11 membered bicyclic aryl ring or 5-6 membered heteroaryl ring is optionally linearly fused to a second 5-6 membered aryl or heteroaryl ring having 0-3 heteroatoms independently selected from N, O, or S;

wherein said 3-7 membered monocyclic or 6-12 membered bicyclic saturated or partially unsaturated carbocyclic ring or said 3-7 membered monocyclic or a 6-12 membered bicyclic heterocyclic ring is optionally spirocyclic or linearly fused to a 4-7 membered saturated or partially unsaturated heterocyclic or carbocyclic ring;

wherein said 4-7 membered saturated or partially unsaturated heterocyclic or carbocyclic fused ring contains 0-3 heteroatoms independently selected from N, $NR^3$, O, S, SO, or $SO_2$; and wherein $Ar^1$ is optionally substituted with 1-3 J groups.

According to another embodiment of any of the methods embodiments described herein, Ring A is a 5-6 membered heteroaryl ring having 1-3 heteroatoms independently selected from N, O, or S;

wherein said 5-6 membered heteroaryl ring system is optionally linearly fused to a second 5-6 membered aryl or heteroaryl ring;

wherein said 5-6 membered aryl or heteroaryl fused ring contains 0-3 heteroatoms independently selected from N, O, or S; and wherein any of said rings is optionally substituted with up to 2 substituents independently selected from J.

According to another embodiment of any of the methods embodiments described herein, L is —$C(O)N(R^4)$ and $R^4$ is hydrogen. In another embodiment, L is —$N(R^4)C(O)$ and $R^4$ is hydrogen.

According to another embodiment of any of the methods embodiments described herein, $R^1$ is hydrogen. In yet another embodiment, $R^1$ is $OR^5$, wherein $R^5$ is —($C_1$-$C_4$)-straight or branched alkyl. In still another embodiment, $R^5$ is methyl, ethyl or isopropyl. In another embodiment, $R^1$ is $OR^5$, wherein $R^5$ is hydrogen.

According to another embodiment of any of the methods embodiments described herein, Q is a bond, t is 1, and $R^2$ is $Ar^1$. In another embodiment, Q is —$C(O)NR^+$ wherein $R^+$ is hydrogen, t is 1, and $R^2$ is $Ar^1$ wherein $Ar^1$ is a 5-6 membered monocyclic or a 7-11 membered bicyclic aryl ring, a 5-6 membered heteroaryl ring having 1-4 heteroatoms independently selected from N, O, or S wherein said 5-6 membered heteroaryl ring is optionally linearly fused to a second 5-6 membered aryl or heteroaryl ring having 0-3 heteroatoms independently selected from N, O, or S and wherein $Ar^1$ is optionally substituted with 1-2 J groups.

According to another embodiment of any of the methods embodiments described herein, t is zero.

According to another embodiment, the present invention provides a method of inhibiting bacterial IMPDH in a patient, comprising administering to said patient a therapeutically effective amount of a compound selected from:

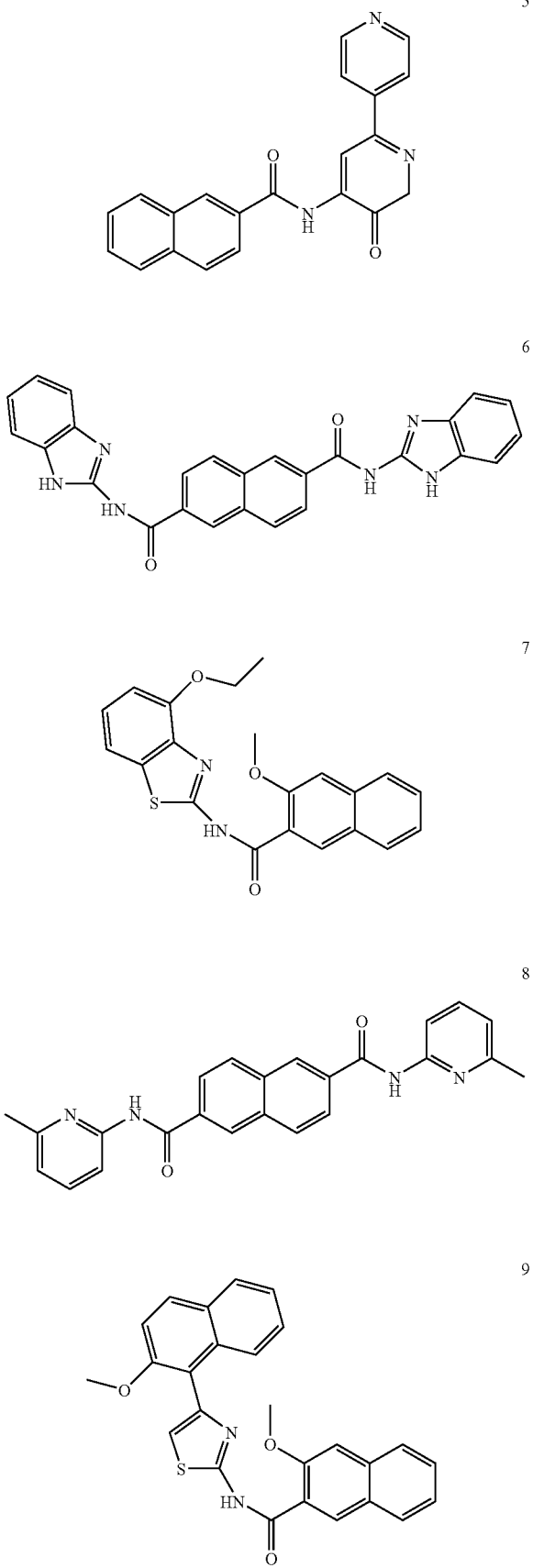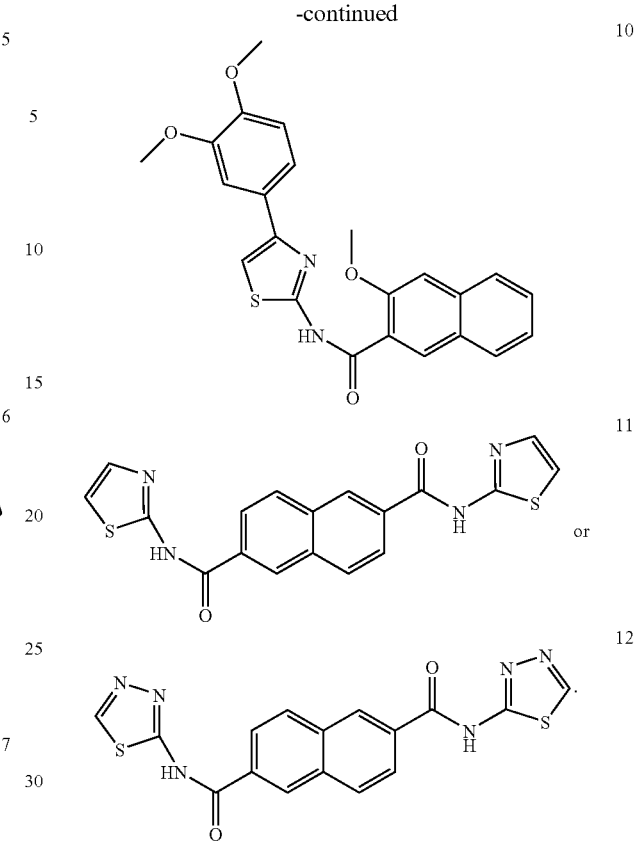

According to another embodiment, the present invention provides a method of inhibiting bacterial IMPDH to decrease bacterial quantity in a patient, comprising administering to said patient a therapeutically effective amount of a compound selected from compound numbers 5, 6, 7, 8, 9, 10, 11 or 12.

According to another embodiment, the present invention provides a method of inhibiting bacterial IMPDH, comprising contacting bacteria with a compound selected from compound numbers 5, 6, 7, 8, 9, 10, 11 or 12

The pharmaceutical compositions and methods of this invention will be useful generally for controlling bacterial infections in vivo. Examples of bacterial organisms that may be controlled by the compositions and methods of this invention include, but are not limited to, the following organisms: *Streptococcus pneumoniae, Streptococcus pyogenes, Enterococcus faecalis, Enterococcusfaecium, Klebsiella pneumoniae, Enterobacter* sps. *Proteus* sps. *Pseudomonas aeruginosa, E. coli, Serratia marcesens, Staphylococcus aureus,* Coag. Neg. Staph, *Haemophilus influenzae, Bacillus anthracis, Mycoplasma pneumoniae, Moraxella catarralis, Chlamydia pneumoniae, Legionella pneumophila, Staphylococcus epidermidis, Mycobacterium tuberculosis, Helicobacter pylori*, Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant

*Mycoplasma*, Isoniazid resistant *Mycobacterium*, Rifampin resistant *Mycobacterium*, or β-lactam resistant *Moraxella*.

According to another embodiment, the present invention provides a method wherein the bacterial infection to be treated is selected from one or more of the following: a urinary tract infection, a respiratory infection, pneumonia, prostatitis, a skin or soft tissue infection, an intra-abdominal infection, a blood stream infection, or an infection of febrile neutropenic patient.

According to another embodiment, the present invention provides a method further comprising the step of administering to said human one or more additional therapeutic agents either as part of a multiple dosage form together with said compound or as a separate dosage form wherein said one or more additional therapeutic agents include an antibiotic selected from a natural penicillin, a penicillinase-resistant penicillin, an antipseudomonal penicillin, an aminopenicillin, a first generation cephlosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidone, a rifamycin, or other antibiotics.

According to another embodiment, said natural penicillin is Benzathine penicillin G, Penicillin G or Penicillin V, said penicillinase-resistant penicillin is Cloxacillin, Dicloxacillin, Nafcillin or Oxacillin, said antipseudomonal penicillin is Carbenicillin, Mezlocillin, Pipercillin, Pipercillin/tazobactam, Ticaricillin or Ticaricillin/Clavulanate, said aminopenicillin is Amoxicillin, Ampicillin or Ampicillin/Sulbactam, said first generation cephalosporin is Cefazolin, Cefadroxil, Cephalexin or Cephadrine, said second generation cephalosporin is Cefaclor, Cefaclor-CD, Cefamandole, Cefonacid, Cefprozil, Loracarbef or Cefuroxime, said third generation cephalosporin is Cefdinir, Cefixime, Cefoperazone, Cefotaxime, Cefpodoxime, Ceftazidime, Ceftibuten, Ceftizoxme or Ceftriaxone, said fourth generation cephalosporin is Cefepime, said Cephamycin is Cefotetan or Cefoxitin, said carbapenem is Imipenem or Meropenem, said monobactam is Aztreonam, said quinolone is Cinoxacin, Nalidixic acid, Oxolininc acid or Pipemidic acid, said fluoroquinolone is Cirpofloxacin, Enoxacin, Gatifloxacin, Grepafloxacin, Levofloxacin, Lomefloxacin, Moxifloxacin, Norfloxacin, Ofloxacin or Sparfloxacin, said aminoglycoside is Amikacin, Gentamicin, Kanamycin, Neomycin, Netilmicin, Spectinomycin, Streptomycin or Tobramycin, said macrolide is Azithromycin, Clarithromycin or Erythromycin, said ketolide is Telithromycin, said Tetracycline is Chlortetracycline, Demeclocycline, Doxycycline, Minocycline or Tetracycline, said glycopeptide is Oritavancin, Teicoplanin or Vancomycin, said streptogramin is Dalfopristin/quinupristin, said oxazolidone is Linezolid, said Rifamycin is Rifabutin or Rifampin and said other antibiotic is bactitracin, chloramphenicol, clindamycin, isoniazid, metronidazole, polymyxin B, pyrazinamide, or trimethoprim/sulfamethoxazole.

In yet another embodiment, said natural penicillin is Penicillin G, said penicillinase-resistant penicillin is Nafcillin or Oxacillin, said antipseudomonal penicillin is Pipercillin/tazobactam, said aminopenicillin is Amoxicillin, said first generation cephalosporin is Cephalexin, said second generation cephalosporin is Cefaclor, Cefaclor-CD or Cefuroxime, said third generation cephalosporin is Ceftazidime or Ceftriaxone, said fourth generation cephalosporin is Cefepime, said fluoroquinolone is Cirpofloxacin, Gatifloxacin, Levofloxacin or Moxifloxacin, said aminoglycoside is Tobramycin, said macrolide is Azithromycin or Clarithromycin, said Tetracycline is Doxycycline, said glycopeptide is Vancomycin, said Rifamycin is Rifampin and said other antibiotic is isoniazid, pyrazinamide, or trimethoprim/sulfamethoxazole.

According to another embodiment, the present invention provides a method that further comprises the step of administering to a patient one or more additional therapeutic agents that increase the susceptibility of bacterial organisms to antibiotics.

According to another embodiment, the invention provides a method of decreasing bacterial quantity in a biological sample.

In another embodiment, the pharmaceutical compositions and methods of this invention will be useful generally for controlling bacterial infections in vivo caused by the following the following organisms: *Streptococcus pneumoniae, Streptococcus pyogenes, Enterococcusfaecalis, Enterococcus faecium, Staphylococcus aureus, Coag. Neg. Staph, Haemophilus infuenzae, Bacillus anthracis, Mycoplasma pneumoniae, Moraxella catarralis, H. influenzae, Chlamydia pneumoniae, Legionella pneumophila, Mycobacterium tuberculosis, Helicobacter pylori, Staphylococcus epidermidis. Chlamydia pneumoniae, Legionella pneumophila, Mycobacterium tuberculosis, Staphylococcus saprophyticus,* or *Helicobacter pylori*.

In another embodiment, the pharmaceutical compositions and methods of this invention will be useful generally for controlling bacterial infections in vivo caused by the following the following organisms: *Streptococcus pneumoniae, Streptococcus pyogenes, Enterococcus faecalis, Enterococcus faecium, Staphylococcus aureus, Coag. Neg. Staph, Bacillus anthracis, Staphylococcus epidermidis, Staphylococcus saprophyticus,* or *Mycobacterium tuberculosis*.

The compositions and methods will therefore be useful for controlling, treating or reducing the advancement, severity or effects of nosocomial or non-nosocomial infections. Examples of nosocomial uses include, but are not limited to, urinary tract infections, respiratory infections such as pneumonia, surgical wound infections, and blood stream infections (also known as bacteremia). Examples of non-nosocomial uses include but are not limited to urinary tract infections, pneumonia, prostatitis, skin and soft tissue infections, intra-abdominal infections, and therapy for febrile neutropenic patients.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

The compounds of formula I may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The additional therapeutic agents described above may be administered separately, as part of a multiple dosage regimen, from the inhibitor-containing composition. Alternatively, these agents may be part of a single dosage form, mixed together with the inhibitor in a single composition.

In order that this invention be more fully understood, the following examples are set forth. These examples are for the purpose of illustration only and are not to be construed as limiting the scope of the invention in any way.

Chemical naming for selected compounds herein was accomplished using the naming program provided by CambridgeSoft Corporations ChemDraw Ultra®, version 7.0.1.

$^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

EXAMPLES

Example 1

N-(2,3-dihydro-3-oxo-6-(pyridin-4-yl)pyridin-4-yl)-2-naphthamide (5)

Compound 5 was prepared according to the method listed in Scheme II above. $^1$H NMR: (DMSO-d6) δ 7.62-769 (4H, m), 7.84 (1H, s), 8.02 (2H, t), 8.10 (1H, d), 8.16 (1H, d), 8.59-8.62 (3H, m), 8.82 (1H, s), 12.65 (1H, s). Mass Spec.: MS+342.5; MS+340.7

Example 2

IMPDH Activity Inhibition Assay

IMP dehydrogenase activity was assayed according to the method reported by Hedstrom. [Hedstrom, L. et al., *Biochemistry*, 39, pp. 9804-9810 (2000), the disclosure of which is herein incorporated by reference]. Table 1 below lists the percent remaining activity of *E. coli* IMPDH enzyme (E) at either 25 µM inhibitor (I) and 14 nM enzyme (E) or 10 µM inhibitor (I) and 55 nM enzyme (E). "ND" means no data.

TABLE 1

| Compound No. | % Activity 25 µM I 14 nM E | % Activity 10 µM I 55 nM E |
|---|---|---|
| 5 | 59% | ND |
| 6 | 90% | ND |
| 7 | 76% | ND |
| 8 | ND | 87% |
| 9 | ND | 100% |
| 10 | ND | 73% |
| 11 | ND | 97% |
| 12 | ND | 100% |

Example 3

Susceptibility Testing in Liquid Media

Compounds of this invention may be tested for antimicrobial activity by susceptility testing in liquid media. Such assays may be performed within the guidelines of the latest NCCLS document governing such practices: "M7-A5 Methods for dilution Antimicrobial Susceptibility Tests for Bacteria that Grow Aerobically; Approved Standard-Fifth Edition (2000)". Other publications such as "Antibiotics in Laboratory Medicine" (Edited by V. Lorian, Publishers Williams and Wilkins, 1996) provide essential practical techniques in laboratory antibiotic testing. Essentially, several discrete bacterial colonies (3-7) of *Staphylococcus aureus* (wild type, ATCC 29213), *E. coli* (tolC mutant; CAG12184 from Coli Genetic Stock Center), or *Haemophilus influenzae* (AcrAB::kn mutant; was the gift of Hiroshi Nikkaido's lab), from a freshly streaked plate may be transferred to an appropriate rich broth medium such as MHB, supplemented where appropriate for the more fastidious organisms. This is grown overnight to high density followed by a 1 or 2-thousand-fold dilution to give an inoculation density of between $5\times10^5$ and $5\times10^6$ CFU per mL. Alternatively, the freshly picked colonies may be incubated at 37° C. for about 4 to 8 hours until the culture equals or exceeds a turbidity of a 0.5 McFarland standard (approximately $1.5\times10^8$ cells per mL) and diluted to give the same CFU per mL as above. In a more convenient method, the inoculum is prepared using a commercially available mechanical device (the BBL PROMPT System) that involves touching five colonies directly with a wand, containing crosshatch grooves at its bottom, followed by suspension of the bacteria in an appropriate volume of saline. Dilution to the appropriate inoculum cell density is made from this cell suspension. The broth used for testing consists of MHB supplemented with 50 mg per L of $Ca^{2+}$ and 25 mg per L of $Mg^{2+}$. Standard dilution panels of control antibiotics is made and stored as in the NCCLS standard M7-A5, the dilution range typically being in the 128 µg per mL to 0.015 µg per mL (by 2-fold serial dilution). The test compound is dissolved and diluted fresh for experimentation on the same day; the same or similar ranges of concentration as above being used. The test compound and control is dispensed into a multiwell plate and test bacteria added such that the final inoculation is approximately $5\times10^4$ CFU per well and the final volume is 100 µL. The plate is incubated at 35° C. overnight (16 to 20 hours) and checked by eye for turbidity or quantitated with a multiwell plate reader. The endpoint minimal inhibitory concentration (MIC) is the lowest concentration of drug at which the microorganism tested (*Staphylococcus aureus* (wild type, ATCC 29213), *E. coli* (tolC mutant), or *Haemophilus influenzae* (AcrAB::kn mutant) does not grow. Such determination is also compared to the appropriate tables contained in the above two publications to ensure that the range of antibacterial activity is within the acceptable range for this standardized assay.

While we have described a number of embodiments of the present invention, it is apparent that our basic constructions may be altered to provide other embodiments which utilize the products and processes of this invention.

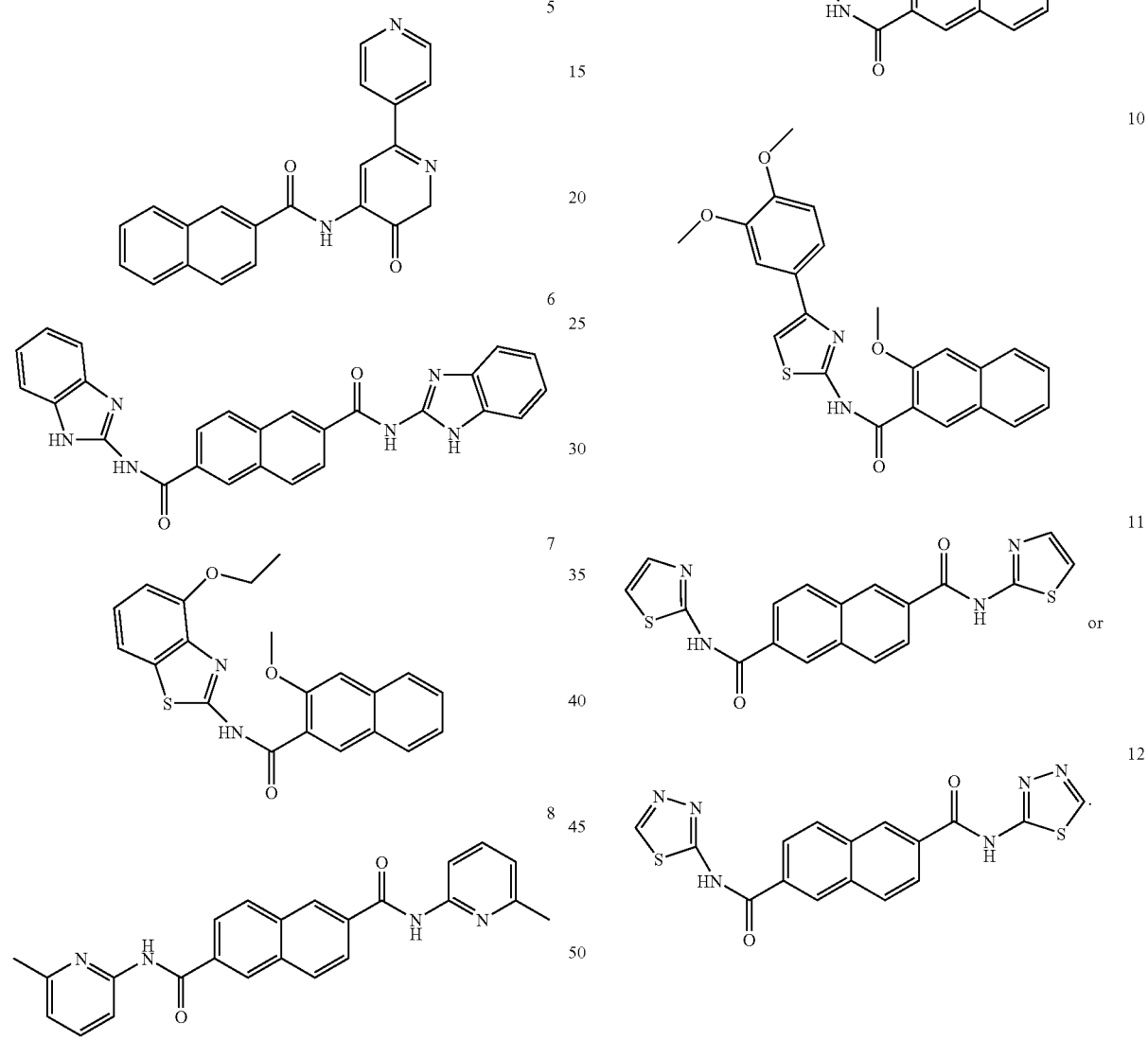

We claim:

1. A method of inhibiting bacterial IMPDH in a patient, comprising administering to said patient a therapeutically effective amount of a compound selected from: